United States Patent
Voss et al.

(10) Patent No.: US 8,828,278 B2
(45) Date of Patent: Sep. 9, 2014

(54) ELECTROPLATING ADDITIVE FOR THE DEPOSITION OF METAL, A BINARY, TERNARY, QUATERNARY OR PENTANARY ALLOY OF ELEMENTS OF GROUP 11 (IB)—GROUP 13 (IIIA)—GROUP 16 (VIA)

(75) Inventors: Torsten Voss, Glienicke/Nordbahn (DE); Jöerg Schulze, Oranienburg (DE); Andreas Kirbs, Potsdam (DE); Aylin Machmor, Riedstadt (DE); Heiko Brunner, Berlin (DE); Bernd Fröese, Berlin (DE); Ulrike Engelhardt, Ketsch (DE)

(73) Assignee: Atotech Deutschland GmbH, Berlin (DE)

( * ) Notice: Subject to any disclaimer, the term of this patent is extended or adjusted under 35 U.S.C. 154(b) by 270 days.

(21) Appl. No.: 12/995,078

(22) PCT Filed: May 29, 2009

(86) PCT No.: PCT/EP2009/003885
§ 371 (c)(1),
(2), (4) Date: Nov. 29, 2010

(87) PCT Pub. No.: WO2009/144036
PCT Pub. Date: Dec. 3, 2009

(65) Prior Publication Data
US 2011/0094583 A1    Apr. 28, 2011

(30) Foreign Application Priority Data
May 30, 2008    (EP) .................................. 08009979

(51) Int. Cl.
*H01B 1/06* (2006.01)
(52) U.S. Cl.
USPC .................................. 252/519.4; 438/584
(58) Field of Classification Search
USPC .............. 252/512, 518.1, 519.14, 500, 519.4; 438/584
See application file for complete search history.

(56) References Cited

U.S. PATENT DOCUMENTS 3,203,878 A    8/1965   Willmund et al.
3,257,294 A *  6/1966   Michael ........................ 205/101

(Continued)

FOREIGN PATENT DOCUMENTS

DE    23 34 355 A1    1/1975
WO    93/02652 A1     2/1993
WO    00/62347 A2    10/2000

OTHER PUBLICATIONS

Fahoume, M., et al., "One, step electrodeposition of Cu(Ga, In)Se2 thin films from aqueous solution," J. Phys. IV France 123 (2005) 75-80.*

(Continued)

*Primary Examiner* — Mark Kopec
*Assistant Examiner* — William Young
(74) *Attorney, Agent, or Firm* — Edwards Wildman Palmer LLP; Peter F. Corless; Mark D. Russett

(57) ABSTRACT

The invention relates to electroplating additives for the deposition of a group IB metal/binary or ternary group IB-group IIIA/ternary, quaternary or pentanary group IB-group IIIA-group VIA alloy on substrates useful for thin film solar cells. The additives are thiourea compounds or derivatives which have the general formula (A):

Formula (A)

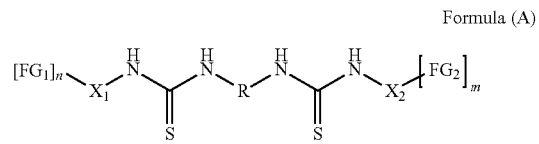

wherein $X_1$ and $X_2$ may be the same or different and are selected from the group consisting of arylene and heteroarylene; $FG_1$ and $FG_2$ may be the same or different or are selected from the group consisting of —S(O)$_2$OH, —S(O)OH, —COOH, —P(O)$_2$OH and primary, secondary and tertiary amino groups and salts and esters thereof; R is selected from the group consisting of alkylene, arylene or heteroarylene and n and m are integers from 1 to 5.

18 Claims, 7 Drawing Sheets

(56) References Cited

U.S. PATENT DOCUMENTS

| | | |
|---|---|---|
| 4,461,821 A | 7/1984 | Sano et al. |
| 5,326,856 A | 7/1994 | Coughlin et al. |
| 5,955,053 A * | 9/1999 | Marzilli et al. ............. 424/1.11 |
| 7,026,258 B2 | 4/2006 | Taunier et al. |
| 7,507,321 B2 * | 3/2009 | Aksu et al. .................... 205/261 |
| 2003/0171561 A1 | 9/2003 | Pillai et al. |
| 2009/0188808 A1* | 7/2009 | Wang et al. ................... 205/261 |

OTHER PUBLICATIONS

Fahoume, M., et al, "One step electrodeposition of Cu(Ga,In)Se2 thin films from aqueous solution," J. Phys. IV France, 123 (2005) 75-80.*

Lincot, D., et al., "Chalcopyrite thin film solar cells by electrodeposition," Solar Energy 77 (2004) 725-737.*

Ganchev, M., et al., "Preparation of Cu(In,Ga)Se2 layers by selenization of electrodeposited Cu—In—Ga precursors," Thin Solid Films, 511-512 (2006) pp. 325-327.*

Bouabid, K., et al., "CuInGaSe2 thin films prepared by one step electrodeposition," J. Phys. IV France, 123 (2005) 53-57.*

D. Lincot et al. "Chalcopyrite thin film solar cells by electrodeposition", Solar Energy, vol. 77, pp. 725-737 (2004).

L. Dai et al., "Doping of Conducting Polymers by Sulfonated Fullerene Derivatives and Dendrimers", J. Phys. Chem., vol. 102, pp. 4049-4053 (1998).

M. Fahoume et al., "One, step electrodeposition of Cu(Ga,In)Se2 thin films from aqueous solution", J.Phys. IV France, vol. 123, pp. 75-80 (2005).

S. Takagi et al., "Studies on the Syntheses of Polymethylene-bisthioureas and their Derivatives", Pharmaceutical Society of Japan, vol. 7, pp. 206-208 (1959).

G.A. Li et al., "Phase transfer catalyzed synthesis of hexandioyl diaryl dithiourea compounds" Chemical Research and Application, 17(2), pp. 237-239 (2005).

M. Fahoume et al., "One, step electrodeposition of Cu(Ga,In)Se2 thin films from aqueous solution", J. Phys. IV France, vol. 123, pp. 75-80 (2005).

* cited by examiner

ELECTROPLATING ADDITIVE FOR THE DEPOSITION OF METAL, A BINARY, TERNARY, QUATERNARY OR PENTANARY ALLOY OF ELEMENTS OF GROUP 11 (IB)—GROUP 13 (IIIA)—GROUP 16 (VIA)

FIELD OF THE INVENTION

The present invention relates to electroplating additives for the deposition of a group IB metal/binary or ternary group IB-group IIIA/ternary, quaternary or pentanary group IB-group IIIA-group VIA alloy on substrates useful for thin film solar cells. Further, the invention relates to a process for the preparation of these additives and their use in a metal plating composition.

BACKGROUND OF THE INVENTION

It is more and more recognised that photovoltaic conversion of solar energy has to become as soon as possible a major source of the world energy supply in the future.

The photovoltaic industry will be a major industry producing solar modules with the square km as a reference area unit. All mature technologies, either based on silicon or on thin film (a-Si, µc-Si, CIGS or CdTe), aim to reach this objective. For this, a key point is to develop large area processing at low module production costs while maintaining, or better, increasing the conversion efficiencies. Junctions based on $Cu(In,Ga,Al)(S,Se)_2$ chalcopyrite absorbers have already demonstrated high conversion efficiencies and compatibility with large area production of efficient modules at the pre-industrial level (D. Lincot et al., Solar Energy 77 (2004) 725-737).

According to WO 00/62347 a solar cell is provided with an absorbing layer which is arranged on a flexible and band-shaped support. The absorbing layer is at least partially provided with components of copper and is provided with at least one element from the group of indium and gallium and with at least one element from the group of selenium and sulphur and is at least partially embodied as p-type. The absorbing layer is at least partially deposited on the support in a plating manner. The components of the absorbing layer are in a stoichiometric ratio in relation to one another. The absorbing layer is heat-treated after having been deposited on the support.

U.S. Pat. No. 7,026,258 B2 concerns a method for making thin-film CIGS which consists in: electrochemically depositing on a substrate a layer of stoichiometry close to $CuInSe_2$; then rapidly annealing said layer from a light source with pulses of sufficient power to recrystallise CIS. The electrodeposited elements are premixed. Thus, after the deposition step, a homogeneous matrix is obtained which can support sudden temperature increases during the rapid annealing.

All these processes involve the preparation of group IB-IIIA-VIA metal alloys and, in particular, alloys comprising copper, indium and selenium.

Coating thin layers of metal by way of electrochemistry is nowadays a well-known and frequently used technique, in particular for depositing copper. Electroless deposition as well as electrodeposition of such a metal has been developed for the purposes of decorative industry, protection against corrosion and for the electronic industry, and has reached a mature stage.

However, the prior art methods for depositing the above mentioned elements suffer from the defect that the ratio of deposited copper to indium is not constant throughout the entire substrate surface. In particular, the variation in the Cu—In atomic ratio is much too high to produce a working solar module on a substrate as large as, for example, 10×10 $cm^2$.

OBJECT OF THE INVENTION

Therefore, it is the object of the present invention to provide a metal plating composition which can be used to uniformly deposit a group IB metal/binary or ternary group IB-group IIIA/ternary, quaternary or pentanary group IB-group IIIA-group VIA alloy wherein the group IB metal/group IIIA metal atomic ratio varies with a small standard deviation only. More particularly, the use of the metal plating composition should avoid inhomogeneities in the aforementioned metal ratio and overall square mass distribution caused by the hydrodynamic, potential and current density conditions of the plating arrangement.

SUMMARY OF THE INVENTION

These objects are achieved by a new additive that is added to the metal plating composition, which additive has the following general formula (A):

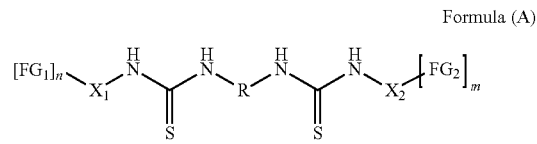

Formula (A)

wherein $X_1$ and $X_2$ may be the same or different and are selected from the group consisting of arylene and heteroarylene;

$FG_1$ and $FG_2$ may be the same or different and are selected from the group consisting of —S(O)$_2$OH, —S(O)OH, —COOH, —P(O)$_2$OH and primary, secondary and tertiary amino groups and salts and esters thereof;

R is selected from the group consisting of alkylene, arylene or heteroarylene and n and m are integers from 1 to 5.

The Cu/In atomic ratio varies with a standard deviation of nearly 16%. Deposition was performed on a 15×15 $cm^2$ molybdenum coated float glass material (centered plotted measurement area 10×10 $cm^2$). The variation in the Cu/In atomic ratio is much too high to produce a working solar cell on that 15×15 $cm^2$ substrate size.

Figure 2:
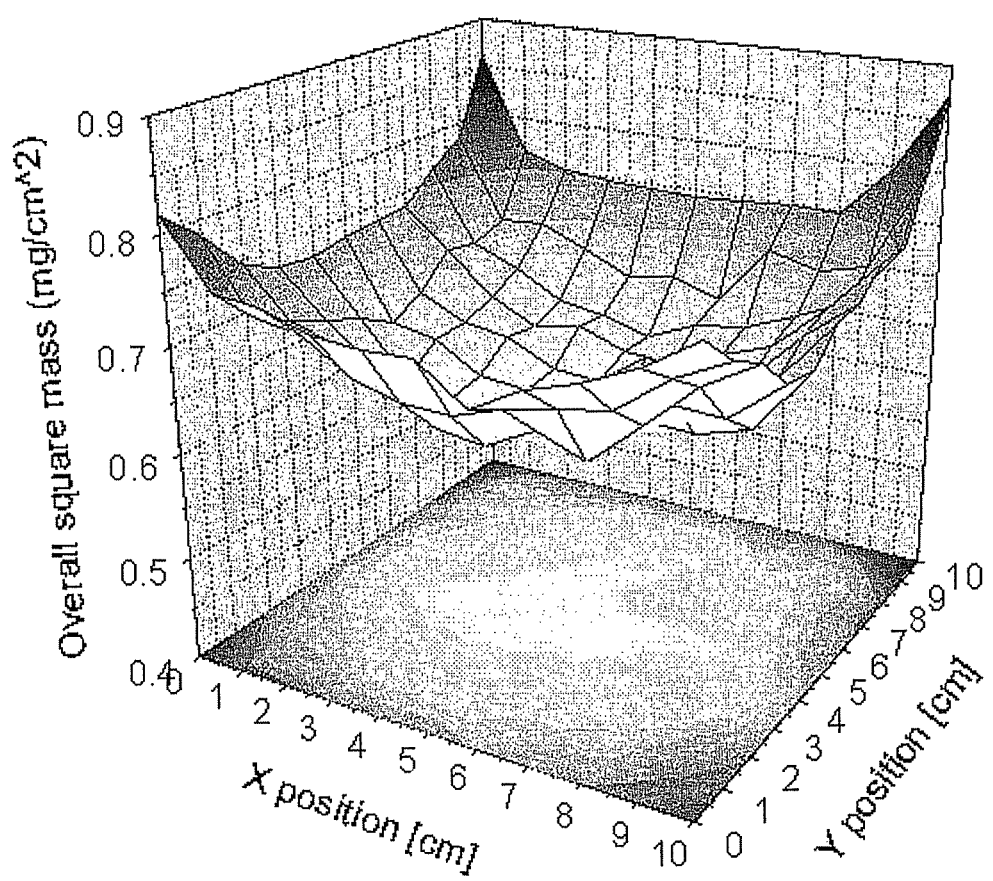

FIG. 2 shows an XRF surface scan and plot of the total layer thickness obtained in Example 2 (not according to the invention).

The total layer thickness of the alloy deposition varies with a standard deviation of more than 8%. The inhomogeneities caused by hydrodynamics, potential and current density drops are clearly visible. Deposition was performed on a 15×15 $cm^2$ molybdenum float glass material (centered plotted measurement area 10×10 $cm^2$).

Figure 3:
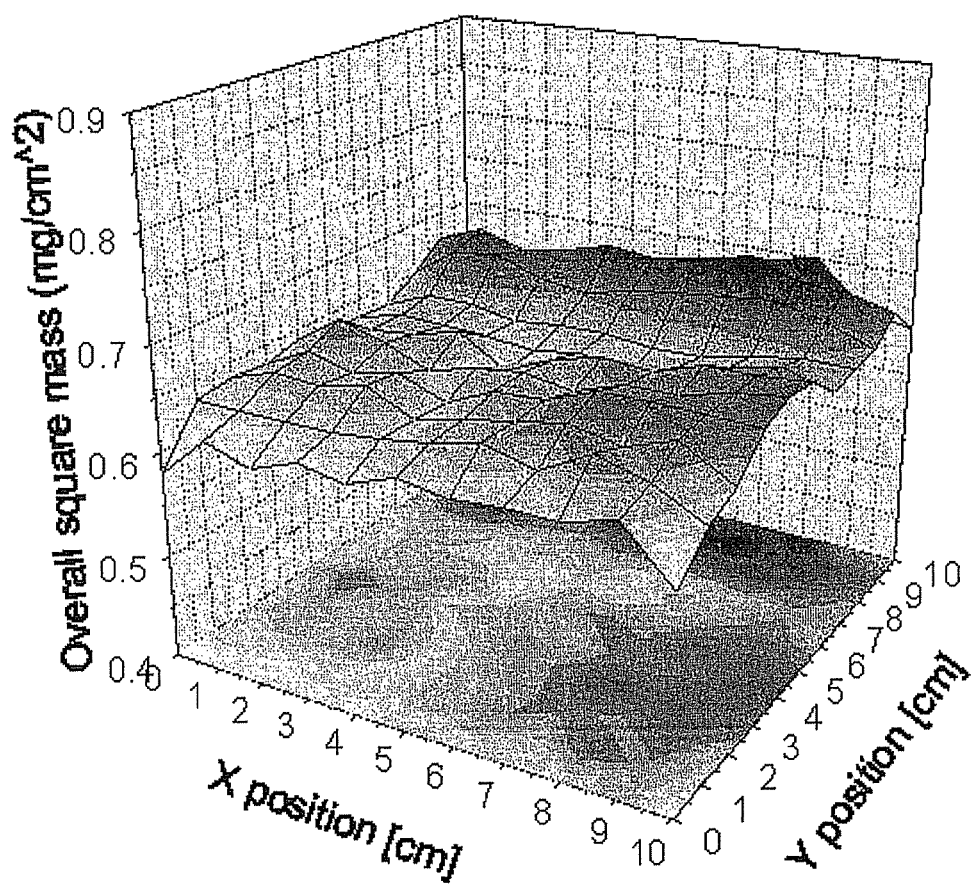

FIG. 3 shows an XRF surface scan and plot of the total layer thickness obtained in Example 1 according the present invention.

The total layer thickness varies with a standard deviation of less than 7%. Deposition was performed on a 15×15 cm² molybdenum coated float glass material (centered plotted measurement area 10×10 cm²). Only mild inhomogeneities caused by hydrodynamics are visible.

Figure 4:
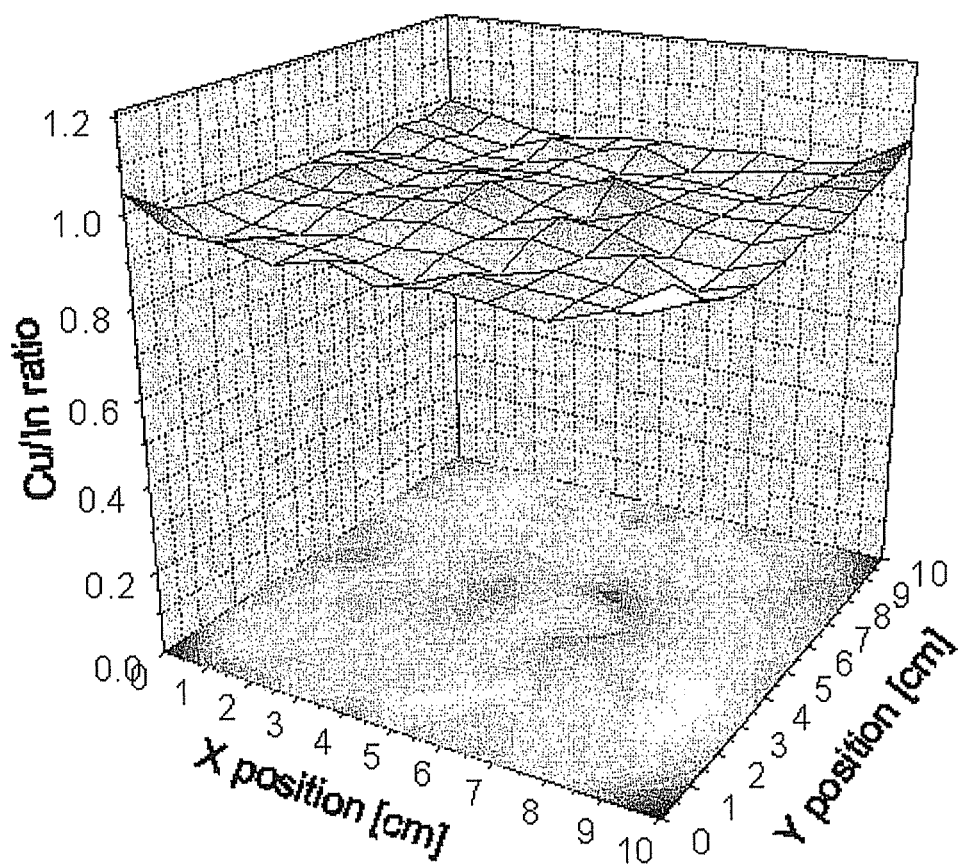

FIG. 4 shows an XRF surface scan and plot of the Cu/In atomic ratio obtained in Example 1 of the present invention.

The Cu/In atomic ratio varies with a standard deviation of less than 3%. Such a variation in atomic ratio is suitable for an industrial production of solar cells. Deposition was performed on a 15×15 cm² molybdenum coated float glass material (centered plotted measurement area 10×10 cm²).

Figure 5:
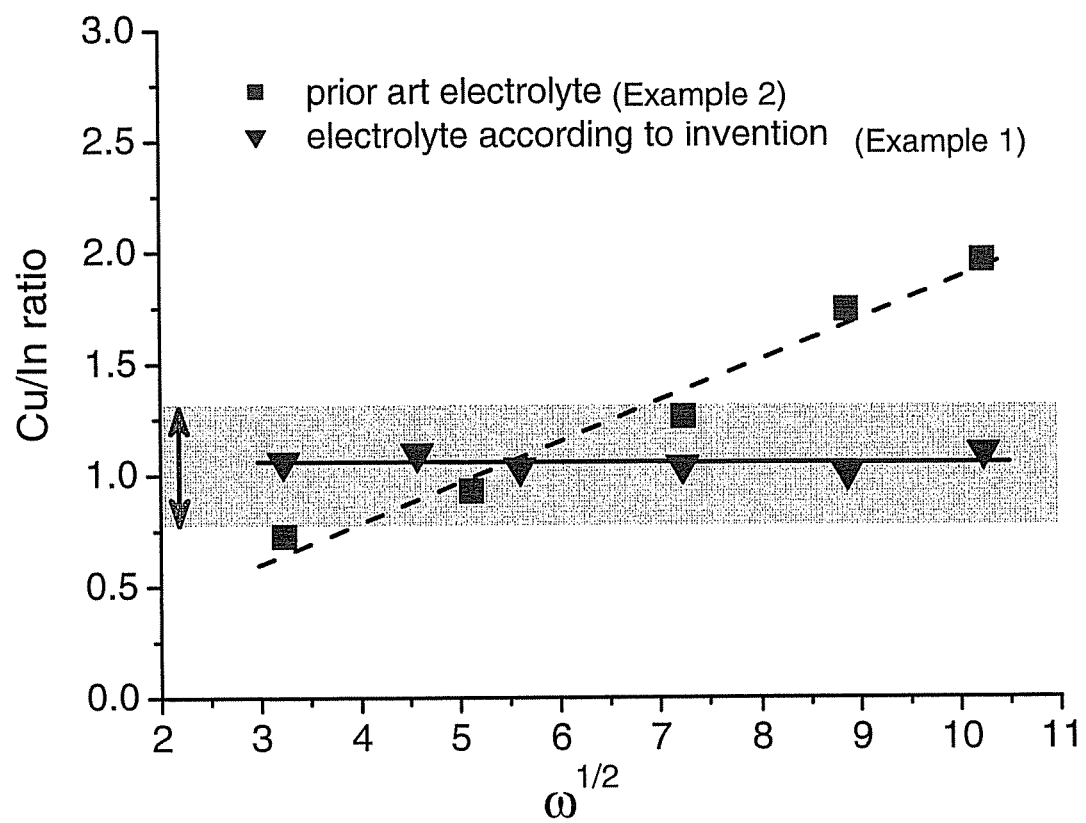

FIG. 5 shows a plot in Levich coordinates (R. G. Compton, C. E. Banks, Understanding Voltammetry; World Scientific Publishing Co. Pte. Ltd (2007)) of a Mo Rotating Disc Electrode (RDE) (dashed/squares—prior art electrolyte: dependence of stoichiometry [Cu/In ratio] from hydrodynamics; solid/triangles—electrolyte according to invention: independence of stoichiometry [Cu/In ratio] from hydrodynamics; potential −1.1 V vs. Ag/AgCl; the stoichiometry [Cu/In ratio] can be shifted within the grey area by proper pH adjustment of the solution). In FIG. 5 ω denotes the rotating frequency of the rotating anode which is a measure for the hydrodynamic conditions in a galvanic bath. According to the Levich equation the square root of ω is directly linked to the current density of the RDE which is according to Faraday's law a measure for the deposited material.

Figures 6A, 6B:
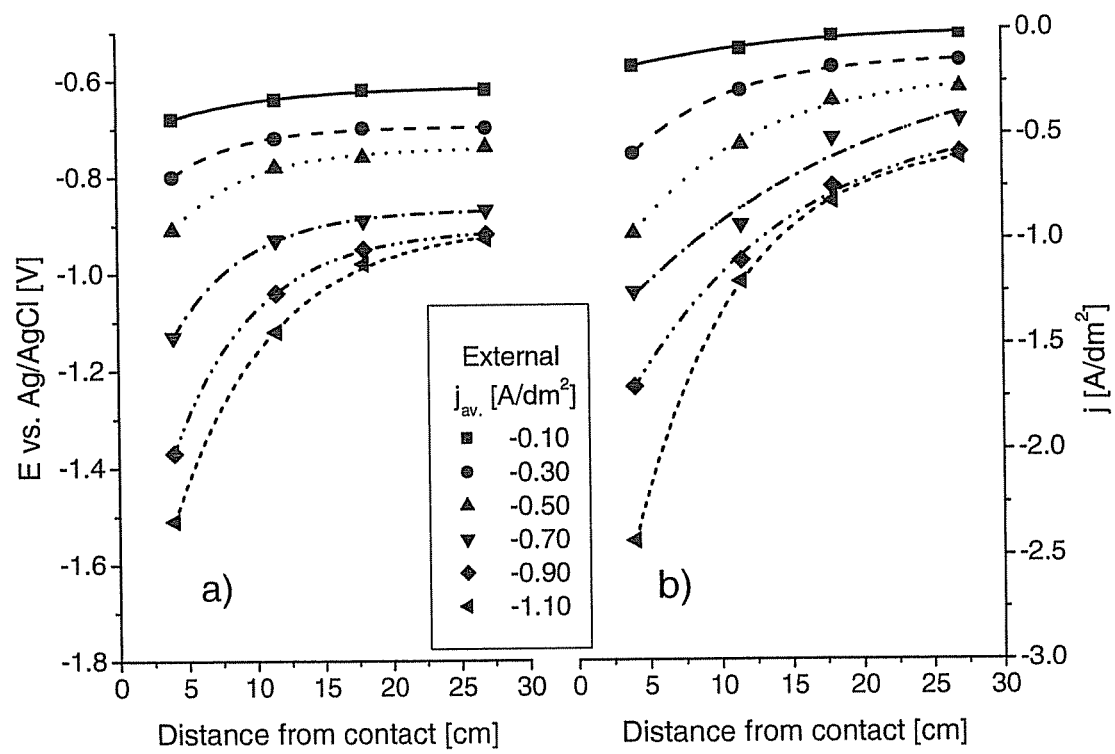

FIG. 6a shows the dependence of the local electrochemical potentials on the distance to the electrical contact on a Mo-coated float glass in relation to the external applied total current density.

FIG. 6b shows the dependence of the local current densities on the distance to the electrical contact on a Mo-coated float glass in relation to the external applied total current density.

Figures 7A, 7B:
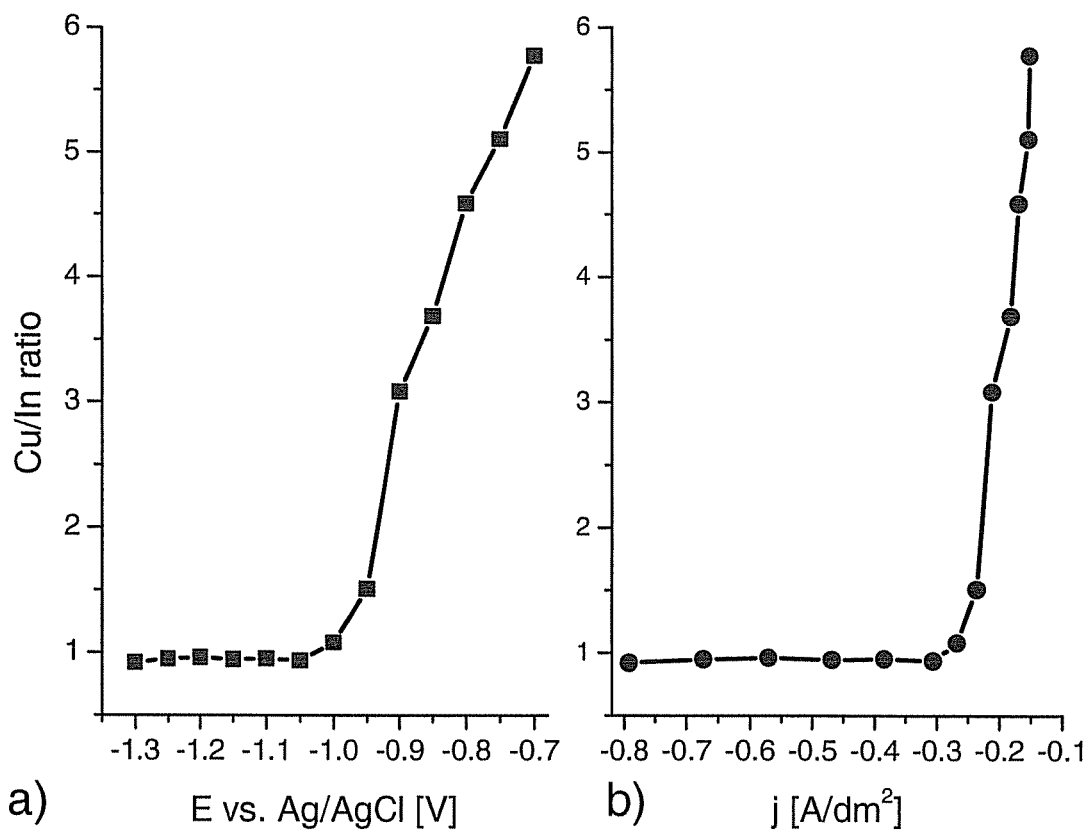

FIGS. 7a and 7b show the stoichiometry (Cu/In ratio) of electrodeposited CISe precursor in relation to a) the applied potential and b) the applied current density on Mo coated float glass as well as the electrolyte behaviour according to invention (Example 1). The horizontal sections of both curves show the ranges wherein a homogeneous alloy composition can be obtained using the additives according to the present invention.

DETAILED DESCRIPTION OF THE INVENTION

Using the additive of the general formula (A) in the plating composition of the invention makes the adjustment of the alloy composition very easy in that said additives importantly influence the alloy composition. The additives may be preferably used in the alloy plating composition, but may also advantageously be used in those plating compositions which are used for preparing the monolayers which together form the sandwich layer.

The additives are preferably selected from the group comprising:

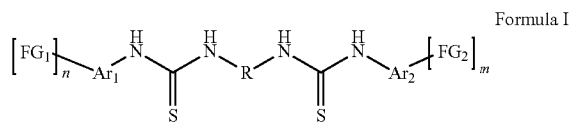

Formula I

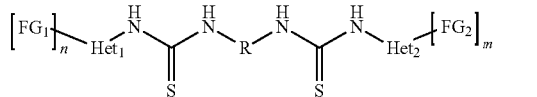

Formula II

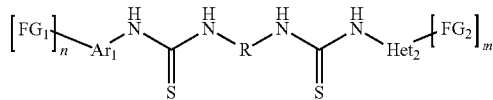

Formula III wherein $Ar_1$, $Ar_2$, $Het_1$, $Het_2$, R, m and n have the same meaning as defined herein before.

The term "arylene", as used herein, means a mono- or polyaromatic divalent radical such as phenylene, benzylene, naphthylene, anthracenylene, adamantylene, phenantracylene, fluoranthenylene, chrysenylene, pyrenylene, biphenylylene, picenylene and the like, including fused benzo-$C_{5-8}$ cycloalkylene radicals such as, for instance, indanylene, 1,2,3,4-tetrahydronaphtalenylene, fluorenylene and the like.

Preferably, $Ar_1$ and $Ar_2$ represent a phenylene or naphthylene radical.

As used herein, the term "heteroaryl" means a mono- or polyheteroaromatic divalent radical including one or more heteroatoms each independently selected from the group consisting of nitrogen, oxygen, sulfur and phosphorus, such as for instance pyridylene, pyrazinylene, pyrimidinylene, pyridazinylene, triazinylene, triazolylene, imidazolylene, pyrazolylene, thiazolylene, isothiazolylene, oxazolylene, pyrrolylene, furylene, thienylene, indolylene, indazolylene, benzofurylene, benzothienylene, quinolylene, quinazolinylene, quinoxalinylene, carbazolylene, phenoxazinylene, phenothiazinylene, xanthenylene, purinylene, benzothienylene, naphtothienylene, thianthrenylene, pyranylene, isobenzofuranylene, chromenylene, phenoxathiinylene, indolizinylene, quinolizinylene, isoquinolylene, phthalazinylene, naphthiridinylene, cinnolinylene, pteridinylene, carbolinylene, acridinylene, perimidinylene, phenanthrolinylene, phenazinylene, phenothiazinylene, imidazolinylene, imidazolidinylene, pyrazolinylene, pyrazolidinylene, pyrrolinylene, pyrrolidinylene and the like, including all possible isomeric forms thereof.

Preferably, $Het_1$ and $Het_2$ are selected from N-containing mono- and poly-heterocycles including pyridylene and quinolinylene.

The groups $FG_1$ and $FG_2$ are substituents for the $Ar_1$, $Ar_2$, $Het_1$ and $Het_2$ radicals and are selected from the group consisting of —$S(O)_2OH$, —$S(O)OH$, —$COOH$, —$P(O)_2OH$ and primary, secondary and tertiary amino groups and salts and esters thereof.

Such salts include the alkaline metal and alkaline-earth metal salts such as sodium, potassium and calcium salts.

Suitable esters are alkyl esters and, in particular, $C_{1-6}$ alkyl esters wherein $C_{1-6}$ alkyl means straight and branched chain saturated hydrocarbon monovalent radicals having from 1 to 6 carbon atoms such as, for example, methyl, ethyl, propyl, n-butyl, 1-methylethyl, 2-methylpropyl, 1,1-dimethylethyl, 2-methylbutyl, n-pentyl, dimethylpropyl, n-hexyl, 2-methylpentyl, 3-methylpentyl, and the like.

Suitable ammonium salts include ammonium ($NH_4^+$) and tetra-n-alkylammonium, like tetra-n-butyl or tetra-n-methyl ammonium salts.

R denotes an arylene or heteroarylene radical as defined herein above. Further, R may be selected from linear or branched alkylene radicals. The alkylene radical has 1 to 20 carbon atoms and includes alkylene radicals derived from the $C_{1-6}$ alkyl groups mentioned above. The term "$C_{1-20}$ alkylene" also includes the higher homologues thereof having 7 to 20 carbon atoms, such as for instance heptylene, ethylhexylene, octylene, nonylene, decylene, dodecylene, octadecylene and the like.

Particularly preferred additives of the present invention are shown below:

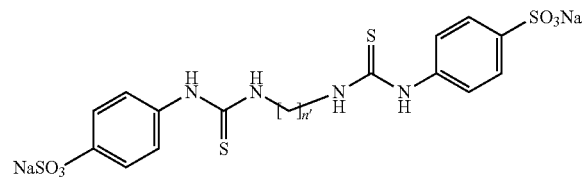

wherein n' is 2 to 12, preferably 2 to 8.

One particularly preferred additive is

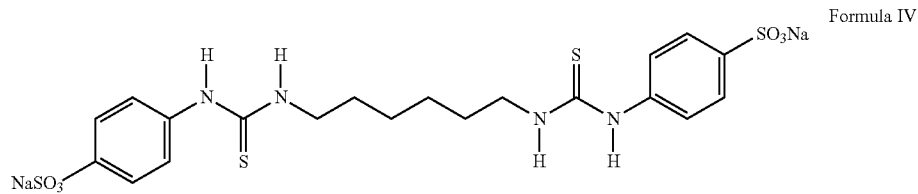

Formula IV

The additives according to the present invention of the general formula (A) can be prepared by a process comprising the step of reacting the following isothiocyanates:

wherein $X_1$, $X_2$, $FG_1$, $FG_2$, m and n are as defined herein before with a diamine compound of the formula $H_2N—R—NH_2$, wherein R is as defined herein before, or reacting the following amine compounds

wherein $Ar_1$, $Ar_2$, $FG_1$, $FG_2$, m and n are as defined herein before with a bis-isocyanate compound of the formula $SCN—R—NCS$, wherein R is as defined herein before.

Likewise, the additives of the general formulae I to III that are contained in the bath according to the invention may be obtained by reaction of the corresponding isothiocyanates with the diamines or by reaction of the bis-isothiocyanates with the corresponding amines. The reaction can be represented by the following exemplified reaction schemes:

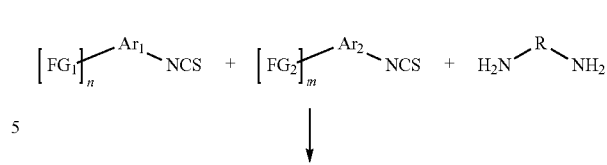

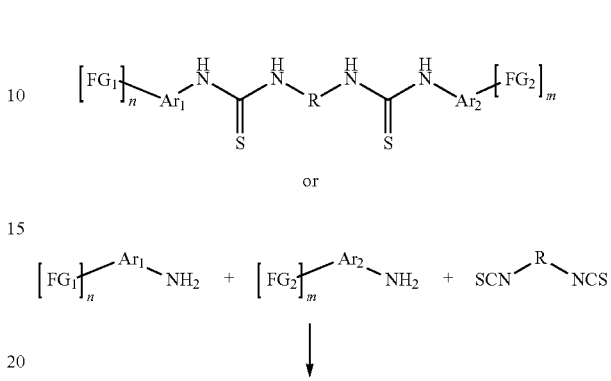

or

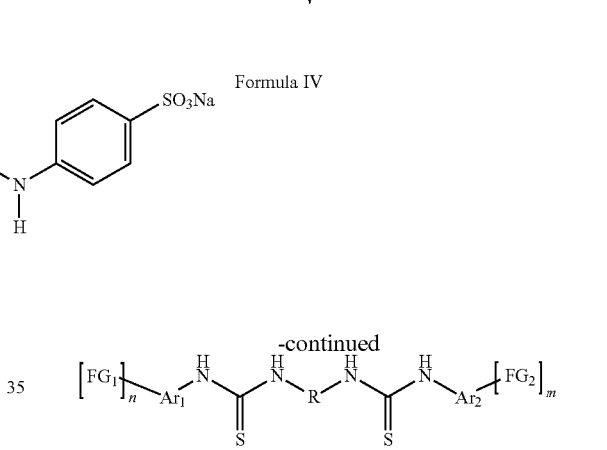

-continued

The preparations may be carried out in aqueous, alcoholic or chlorohalogenated media at ambient or higher temperatures.

According to one embodiment of the invention, the metal plating composition comprises a group IB plating species and a group IIIA plating species and optionally a group VIA plating species.

The group IB plating species preferably comprises copper, the group IIIA plating species comprises gallium and indium and the group VIA plating species comprises selenium and sulfur.

According to another embodiment of the invention, the metal plating composition comprises copper as the group IB plating species, gallium and/or indium as the group IIIA plating species and selenium and/or sulfur as the VIA plating species.

Preferably, the copper, indium and selenium plating species are comprised in the composition at a molar ratio of copper:indium:selenium=1:0.1-50:0.01-40, and most preferred 1:1-5:0.05-2.

The following species are particularly preferred plating species for use in the metal plating composition according to the present invention:
(i) copper plating species
(ii) copper and indium plating species,
(iii) copper, indium and gallium plating species,
(iv) copper, indium and selenium plating species
(v) copper, indium and sulfur plating species (vi) copper, indium, gallium and selenium plating species
(vii) copper, indium, gallium and sulfur plating species and
(viii) copper, indium, gallium, selenium and sulfur plating species.

In general, the metal plating composition according to the present invention comprises the group IB plating species and particularly copper in an amount of 0.5 to 200 mmol/l, preferably 1 to 100 mmol/l and most preferred 3 to 20 mmol/l (either alone or in combination with the group IIIA and, optionally, group VIA plating species).

Suitable amounts for the group IIIA and the group VIA plating species can be calculated from the above molar ratios which are given in an exemplary manner for the plating species copper, indium and selenium.

Preferably, the copper plating species are copper sulphate, copper sulfamates or copper methanesulfamates and the indium plating species are indium sulfamates or indium methansulfamates. In a further preferred embodiment of the present invention, the selenium plating species are comprised of selenous acid.

The metal plating compositions according to the present invention preferably comprise one or more complexing agents including but not limited to citrate and to tartrate complexing agents.

The complexing agents are contained in an amount of 0.001 to 2 mol/l, preferably 0.005 to 1 mol/l and most preferred 0.02 to 0.5 mol/l.

Preferably, the composition further comprises a buffer system.

The buffer system is contained in an amount such that the composition preferably has a pH value of from about 1 to about 6, more preferred from about 1.8 to about 5 and most preferably from about 2.5 to about 4.

Even more preferably, the composition further comprises at least one wetting agent.

To deposit the desired alloy such as a copper-indium-selenium alloy, the substrate is preferably contacted with the metal plating composition at a temperature of from about 15° C. to about 80° C., preferably 20 to 35° C., to form such an alloy.

In order to prepare the layers in accordance with the present invention, the substrate surface to receive such layers will normally be subjected to a pre-cleaning process prior to metallisation. The substrates may be treated before plating with wet-chemical processes developed by the applicant or with any other cleansing chemicals in order to remove any grease, dirt, dust or oxides from the surface. A standard pre-cleaning process is described in Table 1.

TABLE 1

Standard pre-cleaning process

| Bath Name | Treatment Time [s] | Temperature [° C.] | Remarks |
| --- | --- | --- | --- |
| Uniclean ® *) 399 | 180 | 70 | Ultrasonic Activation |
| Uniclean ® *) 260 | 30 | 45 | Ultrasonic Activation |
| Uniclean ® *) 675 | 300 | Room Temperature | Ultrasonic Activation |

*) Trade Mark of Atotech Deutschland GmbH, DE

Uniclean® 399 is a mild alkaline, slightly foaming cleaner, which contains carbonate, silicates, phosphates, tensides and a biodegradable chelating agent. This bath is designed to remove mineral oils, polish and grind residues and pigment impurities for all metals.

Uniclean® 260 is a weak alkaline sodium hydroxide electrolytic cleaner, having electric conductivity, for the use for cathodic or for anodic degreasing.

Uniclean® 675 is an acidic activation agent for universal use. This cleaner contains sodium hydrogensulfate and sodium fluoride.

After having cleaned the substrate, the desired alloy such as a copper-indium-selenium alloy may be deposited on the substrate.

Preferred working conditions are listed below:
temperature: 20-35° C.
pH: 2.5-3.8
current density: 0.3-2 A/dm$^2$
hydrodynamic/electrolyte flow: 0-10 m$^3$/h
deposition speed: 1-20 min
thickness of deposited layer: 0.2-3 μm The deposition can be carried out by direct current plating or by pulse plating with two cathodic potentials (potentiostatic regime). In general, the following potentials can be used for pulse plating: −0.5 to −2 V (potentials measured vs. Ag/AgCl electrode), the pulse times ranging from several tenth of miliseconds to several seconds. As anodes, inert anodes such as the Uniplate typical inert anode can be used.

The additive concentration ranges from 1 to 500 ppm, preferably from 5 to 100 ppm and most preferably from 10 to 50 ppm.

Using such an additive in the metal plating composition according to the present invention enables the preparation of a coated substrate wherein the group IB metal/group IIIA metal atomic ratio varies with a small standard deviation only. Thus, the group IB metal to group IIIA metal ratio obtained by XRF surface plot varies with a standard deviation of less than 4% and preferably less than 2%.

The invention is further illustrated by the following examples:

General Synthetic Procedure 1 of the Inventive Additives 0.2 mol of an isothiocyanat, 0.1 mol of a diamine and 300 mL methanol were added to a reaction flask and the reaction was allowed to proceed at 65° C. for 24 hours until reaction completion. The reaction solution was then cooled to 0° C. and the occurring solid was filtrated and washed with methanol.

The residue was recrystallized from methanol affording white solids.

| Entry | isothiocyanat | diamine | Yield |
| --- | --- | --- | --- |
| 1 | 4-Isothiocyanato-phenyl-sulfonate sodium salt | 1,6-hexanediamine | 74.2% |
| 2 | 4-Isothiocyanato-phenyl-sulfonate sodium salt | 1,4-butanediamine | 58.17% |
| 3 | 4-Isothiocyanato-phenyl-sulfonate sodium salt | 1,8-octanediamine | 58.8% |
| 4 | 4-Isothiocyanato-phenyl-sulfonate sodium salt | ethylendiamin | 89.8% |
| 5 | 4-Isothiocyanato-phenyl-sulfonate sodium salt | N,N-dimethyl-1,6-hexanediamine | 73.5% |
| 6 | 4-Isothiocyanato-phenyl-sulfonate sodium salt | piperazine | 82.8% |
| 7 | 4-Isothiocyanato-phenyl-sulfonate sodium salt | 1,4-phenylendiamine | 81.1% |
| 8 | 6-Isothiocyanato-naphthalene-2-sulfonate sodium salt | 1,6-hexanediamine | 69.35% |
| 9 | 3-Isothiocyanato-pyridine | ethylendiamin | 45.3% |

General Synthetic Procedure 2 of the Inventive Additives 0.2 mol of an amine, 0.1 mol of an diisothiocyanate and 300 mL methanol were added to a reaction flask and the reaction was allowed to proceed at 65° C. for 24 hours until reaction completion. The reaction solution was then cooled to 0° C. and the occurring solid was filtrated and washed with methanol.

The residue was recrystallized from methanol affording white solids.

| Entry | diisothiocyanate | amine | yield |
|---|---|---|---|
| 1 | 2,6-Diisothiocyanato-pyridine | Sulfanilc acid sodium salt | 49.6% |
| 2 | 1,6-Diisothiocyanato-hexane | Sulfanilc acid sodium salt | 35.2% |
| 3 | 1,2-Diisothiocyanato-ethane | Sulfanilc acid sodium salt | 52.8% |

Example 1

A 15×15 cm² molybdenum float glass material was pre-cleaned using the treatment listed in table 1.

Next, a metal plating solution was prepared, the composition of which is shown below:

| 1M | sulfamic acid |
|---|---|
| 1M | sodium hydroxide |
| 0.3M | di-natrium-tartrate |
| 1 mM | selenium(IV)-dioxide |
| 20 mM | indium sulfamate |
| 9 mM | copper sulfamate |
| 40 mg/l | additive according to formula IV |
| 20 µl/l | Lutensit TC-CS40 (tenside) |

The above substrate was immersed into this metal plating solution and an Cu/In/Se alloy was electrolytically deposited on the substrate using the following working conditions:

Temperature: 25° C.
pH: ~3.2
DC-current: current density 1.3 A/dm²
High hydrodynamic/electrolyte flow up to 10 m³/h, hole nozzle array—needed for high deposition speed of ~3 min for 1.5 µm solar cell absorber
Inert anode (Uniplate typical inert anode)

Example 2

Not According to the Invention

A 15×15 cm² molybdenum coated float glass material was pre-cleaned in the same manner as described in Example 1 above.

Further, a metal plating solution was prepared, the composition of which is shown below:

| 1M | sulfamic acid |
|---|---|
| 1M | sodium hydroxide |
| 16 mM | tri-natrium-citrate |
| 12 mM | selenium(IV)-dioxide |
| 50 mM | indium sulfamate |
| 3 mM | copper sulfamate |
| 20 µl/l | Lutensit TC-CS40 (tenside) |

The above substrate was immersed in this metal plating solution and a Cu/In/Se alloy was deposited on the substrate using the following working conditions:

Temperature: 25° C.
pH: ~2.3
Pulse plating with two cathodic potentials (potentiostatic regime): −0.75 V for 0.9 s/−1.1 V for 0.1 s (potentials measured vs. Ag/AgCl electrode)
hydrodynamic/electrolyte flow up to 600 l/h, hole nozzle array
speed of ~15 min for 1.5 µm solar cell absorber
Inert anode (Uniplate typical inert anode)

Example 3

A 15×15 cm² molybdenum coated float glass material was pre-cleaned in the same manner as described in Example 1 above.

Further, a metal plating solution was prepared, the composition of which is shown below:

| 1M | methane sulfonic acid |
|---|---|
| 1M | sodium hydroxide |
| 13.6 mM | tri-natrium-citrate |
| 6 mM | selenium(IV)-dioxide |
| 50 mM | indium hydroxide |
| 50 mM | gallium hydroxide (or as sulfate or chloride) |
| 3 mM | copper oxide |
| 40 mg/l | additive according to formula IV |
| 20 µl/l | CUD 50 (tenside) |

The above substrate was immersed in this metal plating solution and a Cu/In/Se alloy was deposited on the substrate using the following working conditions:

Temperature: 25° C.
pH: ~1.5
Pulse plating with two cathodic potentials (potentiostatic regime): −0.75 V for 0.9 s/−1.1 V for 0.1 s (potentials measured vs. Ag/AgCl electrode)
hydrodynamic/electrolyte flow up to 600 l/h, hole nozzle array
speed of ~15 min for 1.5 µm solar cell absorber
Inert anode (Uniplate typical inert anode)
Results and Evaluation The alloys obtained in Examples 1 to 2 were subjected to a XRF surface scan.

The XRF (x-ray fluorescence) analysis is a non-destructive method. The used equipment (MicroXR 1200SV from Thermo-Fisher-Scientific, USA) has a x-y-table of 30×30 cm². It has a tungsten tube installed. The accelerating voltage is 47 keV. It is equipped with a polycapillary (ø3 mil; ~76 µm). The silicon drift detector (SDD) has a resolution of 163.3 eV (FWHM of Mn-Kα) and is Peltier cooled. The samples are exposed to air, but due to a special geometric configuration and the evacuated beam and detector tubes it is possible to measure elements down to aluminium.

The analysis of thin alloy film (1-2 µm) deposited on the 400 nm molybdenum coated float glass is a complex task. A calibration with pure elemental standard is insufficient. The own preparation of binary, ternary, quaternary or pentanary standards was necessary. They were cross analysed by ICP-OES/ICP-MS.

Figure 1:
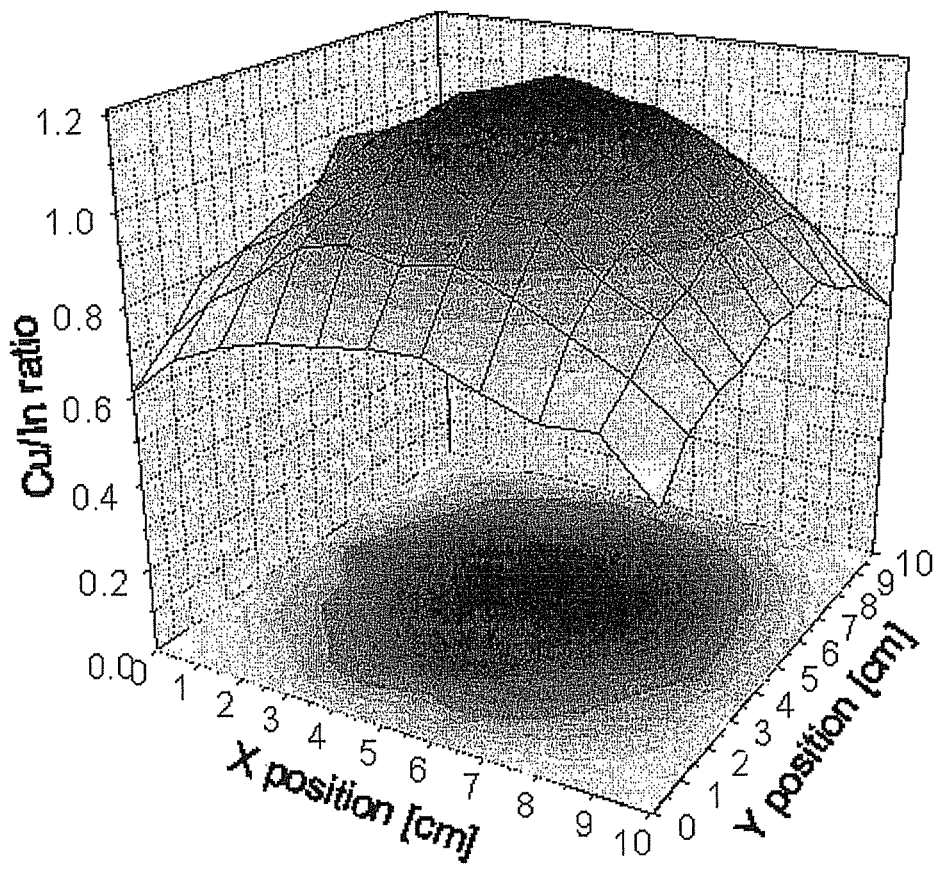
FIG. 1 shows an XRF surface scan and plot of the Cu/In atomic ratio of a metal coating obtained from the prior art electrolyte described in Example 2 (not according to the invention).

As a result, the Cu/In atomic ratio and overall square mass distribution could be determined throughout the entire substrate surface and the corresponding plots are shown in FIGS. 1 and 4 for the alloys obtained in Examples 1 and 2. FIG. 1 shows the Cu/In atomic ratio of the alloy obtained in Example 2 where no additive according to the present invention was contained in the metal plating bath. It is apparent from FIG. 1 that the Cu/In atomic ratio varies with a standard deviation of nearly 16%. Such a variation in the Cu/In atomic ratio is much too high to produce a working solar cell on a 10×10 cm² substrate size (centered cut off a 15×15 cm² substrate—avoiding influences due to the inhomogeneities directly at the electrical contact).

FIG. 4 shows the corresponding plot of the Cu/In atomic ratio obtained from an XRF surface scan of the alloy obtained in Example 1 which is according to the present invention. It is apparent from FIG. 4 that the Cu/In atomic ratio varies with a standard deviation of less then 3%.

Such a variation in the Cu/In atomic ratio is acceptable for producing a working solar module on a 10×10 cm² substrate size.

On the basis of the XRF surface scan, the overall square mass (in mg/cm²) for the alloys obtained in Examples 1 and 2 was plotted and is shown in FIG. 2 (for Example 2) and FIG. 3 (for Example 1).

It is apparent from FIG. 2 that the total layer thickness of the alloy obtained in Example 2 (wherein no additive according to the invention is contained) varies with a standard deviation of more than 8%.

On the other hand, the total layer thickness of the alloy obtained in Example 1 (according to the invention) varies with a standard deviation of less than 7%. The inhomogeneity caused by the hydrodynamic conditions and the potential drop within the Mo substrate are by far less pronounced than in the alloy of Example 2.

FIG. 5 shows the Cu/In ratio of the alloys obtained using the metal plating bath according to Example 1 and Example 2 as a result of varying rotating frequencies of the rotating disc electrode used. In particular, the square root of the rotating frequency (ω) is a measure for the hydrodynamic conditions within a galvanic bath. FIG. 5 confirms that the Cu/In ratio does not depend on the hydrodynamic conditions when a plating bath is used which comprises the additive according to the present invention (Example 1). On the other hand, if such an additive is not present (as in Example 2), the Cu/In ratio depends on the rotating frequency and thus on the hydrodynamic conditions that are present in the plating bath.

FIG. 5 also shows that it is possible to vary the Cu/In ratio obtained in Example 1 (comprising the additive of the present invention) by varying the pH of the plating bath. A lower pH corresponds to a lower Cu/In ratio and a higher pH corresponds to a higher Cu/In ratio, respectively.

FIGS. 6a and 6b show the variation of a) the local electrochemical potential and b) the local current densities as a result of the external applied total current density. These values are measured directly on the Mo-coated float glass substrate at different distances to the electrical contact. The curves shown in FIGS. 6a and 6b explain why the Cu/In ratio considerably increases with increasing distance from the electrical contact when a prior art plating bath is used for the deposition of a Cu—In—Se alloy (cf. FIGS. 1 and 3). In (which is less noble than Cu) is deposited in a smaller content when compared to Cu as a result of the lower potential. The additives according to the present invention are able to compensate for this effect (cf. FIGS. 3 and 4) and to balance the irregularities in the hydrodynamic conditions (cf. FIG. 5).

The curves shown in FIGS. 6a and 6b are typical for the substrate used in this application. Accordingly, the same effect will occur with substrate sizes used on an industrial scale.

Finally, FIGS. 7a and 7b show the stoichiometry (Cu/In ratio) of electrodeposited CISe precursor in dependence of a) applied potential and b) applied current density on Mo coated float glass as well as the electrolyte behaviour according to the invention (Example 1). The horizontal sections in both curves show the operating range wherein a constant alloy composition can be achieved using the additives according to the present invention.

Example 4

The inventive additive according to formula IV was used for deposition of copper in a low acid copper bath with the following composition:

| | |
|---|---|
| 35 g/l | sulphuric acid |
| 35 g/l | copper sulphate pentahydrate |
| 100 ppm | chloride |
| 100 ppm | propylene glycol |
| 20 mg/l | additive according to formula IV |

A brass substrate was coated with copper in a hull cell with a total current of 1.5 A. The deposition time was 300 s.

A homogeneous and bright copper deposit was obtained with the additive according to formula IV.

The invention claimed is:

1. A process for coating a substrate with a binary or ternary group IB-group IIIA/ternary, quaternary or pentanary group IB-group IIIA-group VIA alloy comprising the following steps:
   (i) pre-cleaning the substrate to be coated and
   (ii) contacting the pre-cleaned substrate with a metal plating composition comprising an additive of the general formula (A) in a concentration range from 1 to 500 ppm:

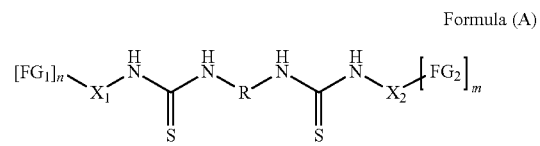

Formula (A)

wherein $X_1$ and $X_2$ may be the same or different and are selected from the group consisting of arylene and heteroarylene;

$FG_1$ and $FG_2$ may be the same or different and are selected from the group consisting of —S(O)$_2$OH, —S(O)OH, —COOH, —P(O)$_2$OH and primary, secondary and tertiary amino groups and salts and esters thereof;

R is selected from the group consisting of alkylene, arylene or heteroarylene and n and m are integers from 1 to 5; and further comprising a group IB plating species and a group IIIA plating species, and a buffer system in an amount such that the composition has a pH value from about 1 to about 6, at a temperature from about 15° C. to about 80° C. to obtain a substrate coated with a binary or ternary group IB-group IIIA/ternary, quaternary or pentanary group IB-group IIIA-group VIA alloy.

2. The process according to claim 1 wherein the additive is selected from the group consisting of compounds having the general formula (I) to (III):

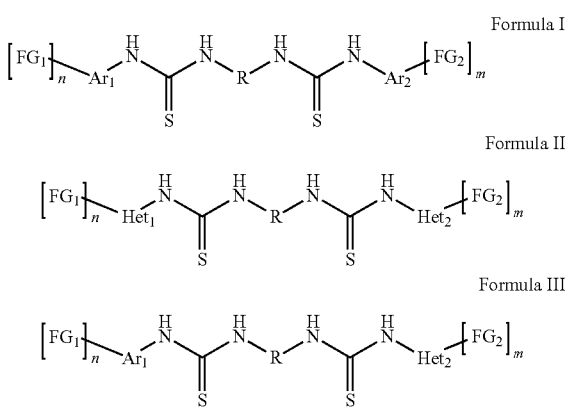

Formula I

Formula II

Formula III wherein $Ar_1$ and $Ar_2$ are the same or different and independently denote an arylene group;

wherein $Het_1$ and $Het_2$ are the same or different and denote a heteroarylene group and wherein $FG_1$, $FG_2$, m and n are defined as in claim 1.

3. The process according to claim 2 wherein $Ar_1$ and $Ar_2$ denote a phenylene or naphthylene group.

4. The process according to claim 2 wherein $Het_1$ and $Het_2$ denote a pyridylene or quinolinylene group.

5. The process according to claim 2 wherein the additive has the formula

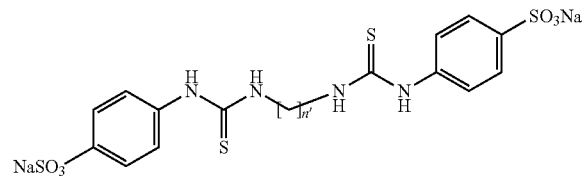

wherein n' is 2 to 12.

6. The process according to claim 1 wherein the metal plating composition further comprises a group VIA plating species.

7. The process according to claim 1 wherein the group IB plating species comprises copper, wherein the group IIIA plating species comprises gallium and/or indium and wherein the VIA plating species comprises selenium and/or sulfur.

8. The process according to claim 7 wherein the metal plating composition comprises plating species selected from:
(i) copper plating species,
(ii) copper and indium plating species,
(iii) copper, indium and gallium plating species,
(iv) copper, indium and selenium plating species,
(v) copper, indium and sulfur plating species,
(vi) copper, indium, gallium and selenium plating species,
(vii) copper, indium, gallium and sulfur plating species and
(viii) copper, indium, gallium, selenium and sulfur plating species.

9. The process according to claim 8 wherein the copper and indium plating species are comprised in the composition in a molar ratio of copper:indium of 1:0.1-50 and wherein the copper and selenium plating species are comprised in the composition in a molar ratio of copper:selenium of 1:0.01-40.

10. The process according to claim 9 wherein the copper and indium plating species are comprised in the composition in a molar ratio of copper:indium of 1:1-5 and wherein the copper and selenium plating species are comprised in the composition in a molar ratio of copper:selenium of 1:0.05-2.

11. The process according to claim 7 wherein the copper plating species are selected from copper sulphate, copper sulfamates and copper methane sulfonates and wherein the indium plating species are selected from indium sulfamates and indium methane sulfamates.

12. The process according to claim 1 wherein the composition has a pH value from about 1.8 to about 5.

13. The process according to claim 1 wherein the composition has a pH value from about 2.5 to about 4.

14. The process according to claim 1 wherein the additive is present in a concentration range of 5 to 100 ppm.

15. The process according to claim 1 wherein the additive is present in a concentration range of 10 to 50 ppm.

16. The process according to claim 1 wherein the composition further comprises a complexing agent in an amount of 0.001 to 2 mol/l.

17. The process according to claim 16 wherein the complexing agent is present in an amount of 0.005 to 1 mol/l.

18. The process according to claim 16 wherein the complexing agent is present in an amount of 0.02 to 0.5 mol/l.

* * * * *